United States Patent
Heinzerling

[11] Patent Number: 6,099,507
[45] Date of Patent: Aug. 8, 2000

[54] INFUSION CATHETER

[75] Inventor: Jörg Heinzerling, Bad Hersfeld, Germany

[73] Assignee: Clinicomed AG, Wilen b. Wollerau, Switzerland

[21] Appl. No.: 09/208,076

[22] Filed: Dec. 9, 1998

[30] Foreign Application Priority Data

Dec. 19, 1997 [DE] Germany .................. 297 22 447 U

[51] Int. Cl.[7] .................................................. A61M 5/32
[52] U.S. Cl. ................................. 604/174; 128/DIG. 26
[58] Field of Search ............................ 604/174, 177, 604/179, 180, 264, 272, 273; 128/DIG. 26

[56] References Cited

U.S. PATENT DOCUMENTS

| | | | |
|---|---|---|---|
| 3,194,235 | 7/1965 | Cooke | 604/180 |
| 3,487,837 | 1/1970 | Petersen | 604/180 |
| 3,782,377 | 1/1974 | Rychlik | 128/DIG. 26 |
| 4,129,128 | 12/1978 | McFarlane | 604/174 |
| 4,397,641 | 8/1983 | Jacobs | 128/DIG. 26 |
| 4,632,671 | 12/1986 | Dalton . | |
| 4,645,495 | 2/1987 | Vaillancourt . | |
| 4,675,006 | 6/1987 | Hrushesky | 128/DIG. 26 |
| 4,710,176 | 12/1987 | Quick | 128/DIG. 26 |
| 5,545,143 | 8/1996 | Fischell . | |
| 5,693,018 | 12/1997 | Kriesel et al. . | |
| 5,858,005 | 1/1999 | Kriesel | 128/DIG. 26 |

FOREIGN PATENT DOCUMENTS

| | | |
|---|---|---|
| 0168289 | 1/1986 | European Pat. Off. . |
| 295 03 099 U | 5/1995 | Germany . |

*Primary Examiner*—Sharon Kennedy
*Attorney, Agent, or Firm*—Friedrich Kueffner

[57] ABSTRACT

An infusion catheter with a cannula embedded in a body of synthetic material, wherein one end of the cannula is connected to a supply line and the other end of the cannula forms the insertion end. The body of synthetic material has a relieving groove in the area where the insertion end of the cannula emerges from the body of synthetic material. The relieving groove may be an annular space whose axis coincides approximately with the cannula in such a way that the annular space extends around the insertion end of the cannula.

3 Claims, 1 Drawing Sheet

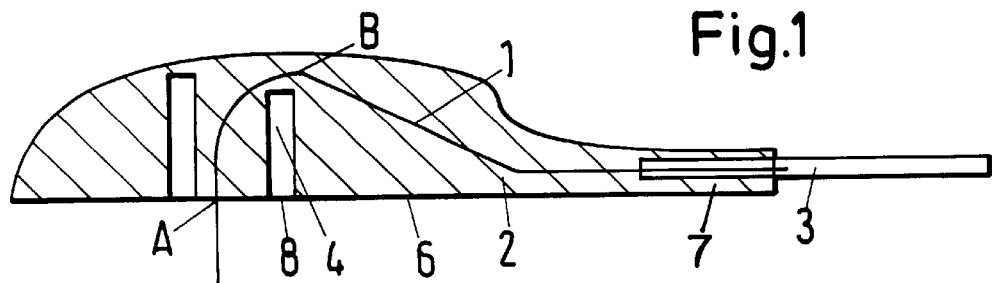
Fig.1
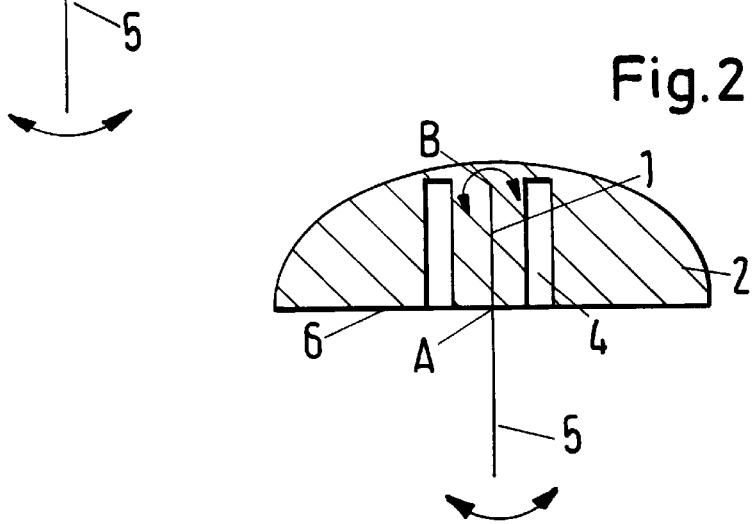
Fig.2
Fig.3
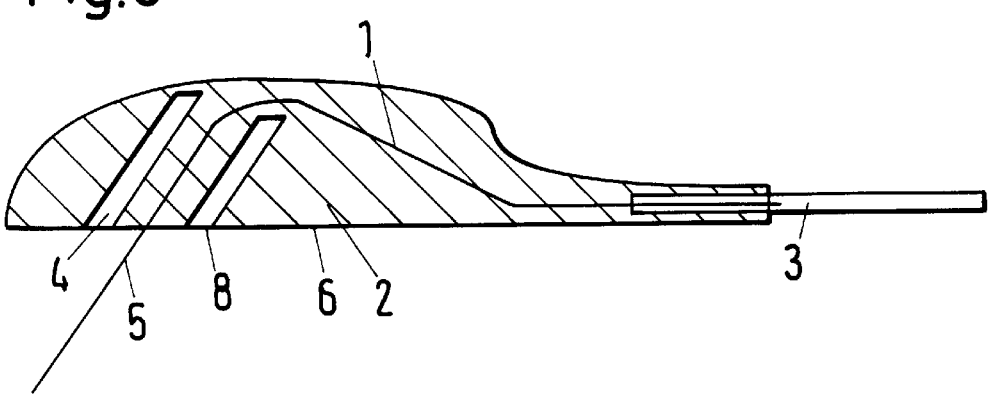
Fig.4
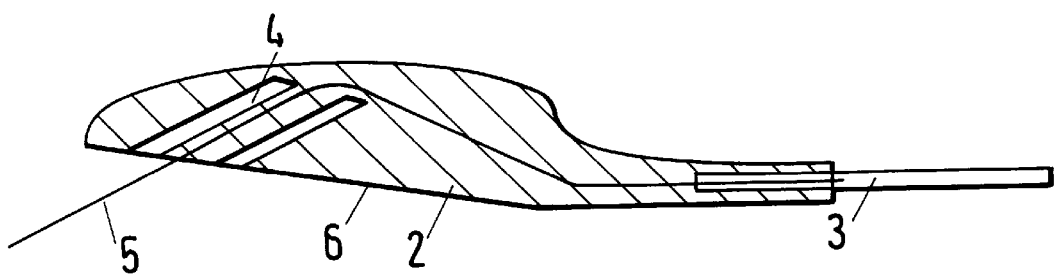

INFUSION CATHETER

BACKGROUND OF THE INVENTION

1. Field of the Invention

The present invention relates to an infusion catheter with a cannula embedded in a body of synthetic material, wherein one end of the cannula is connected to a supply line and the other end of the cannula forms the insertion end.

2. Description of the Related Art

Infusion catheters of the above-described type are used for administering medicaments. They remain in the patient over a longer period of time. In order to reduce trauma of the patient when the catheter is inserted and to minimize the residual volume of the medicament, and for facilitating a rapid healing of the wound, the cross-sections of the cannulas used become smaller and smaller. This means that there is an increasing danger that the cannula will bend or buckle.

SUMMARY OF THE INVENTION

Therefore, it is the primary object of the present invention to provide an infusion catheter of the above-described type in which the cannula does have a small cross-section, but the danger of bending or buckling of the cannula is kept low.

In accordance with the present invention, the body of synthetic material has a relieving groove in the area where the insertion end of the cannula emerges from the body of synthetic material.

As a result of the configuration according to the present invention, the insertion end of the cannula does not emerge without transition in a clamped manner from the body of synthetic material, but the relieving groove provided in the body of synthetic material ensures that the forces transmitted to the insertion end are gradually transferred as bending forces and torsional forces into the body of synthetic material. The same is true with respect to the transmission of forces when the cannula is placed in the patient. Any bending forces acting transversely of the longitudinal axis of the insertion end are converted into torsional forces in the angled portion of the cannula. This also does not occur suddenly, but with a gradual transition.

In accordance with a feature of the present invention, the relieving groove is constructed as an annular space whose axis coincides approximately with the cannula in such a way that the annular space extends around the insertion end of the cannula.

In accordance with a preferred embodiment, the annular space forming the relieving groove extends into the area of the angled portion of the cannula. This produces for the cannula a point of rotation which supports the gradual transmission and conversion of the bending forces.

In accordance with another feature, the annular space is closed at a contact surface of the body of synthetic material with a thin protective skin. The protective skin ensures that the penetration of germs is prevented.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWINGS

In the drawings:

FIG. 1 is a longitudinal sectional view of an embodiment of an infusion catheter according to the present invention;

FIG. 2 is a transverse cross-sectional view of the infusion catheter of FIG. 1;

FIG. 3 is a longitudinal sectional view, corresponding to FIG. 1, of a modified embodiment of the infusion catheter; and FIG. 4 is a longitudinal sectional view corresponding to FIGS. 1 and 3, of another embodiment of the infusion catheter according to the present invention.

DESCRIPTION OF THE PREFERRED EMBODIMENTS

The infusion catheter illustrated in FIG. 1 of the drawing is composed of a thermoplastic body 2. A cannula 1 is embedded and connected in a positively engaging manner in the body 2. The end of the cannula 1 which emerges from the projection 7 of the body 2 is tightly connected to a supply hose 3.

The other end of the cannula 1, which forms the insertion end 5, emerges from the contact surface 6 of the body 2. In the embodiment according to FIGS. 1 and 2, the insertion end 5 extends essentially perpendicularly of the contact surface 6. Within the body 2, the cannula 1 forms an angle, wherein the angle is approximately a right angle. The location where the right angle is formed is denoted by B. The point where the insertion end 5 of the cannula 1 emerges is denoted by A.

Starting from the contact surface 6, a relieving groove in the form of an annular space 4 is provided around the cannula 1. This annular space 4 extends close to the vicinity of the opposite surface of the body 2. The annular space 4 is somewhat shorter only where the angled cannula 1 is located.

The embodiments according to FIGS. 3 and 4 differ from the embodiment of FIGS. 1 and 2 in that the insertion end 5 does not extend precisely at a right angle relative to the contact surface 6, but extends at an angle of somewhat more than 90° relative to the end of the body 2 where the projection 7 is provided.

In the embodiment of FIG. 4, the projection 7 does not extend exactly parallel to the contact surface 6. In this embodiment, the contact surface 6 is somewhat inclined relative to the projection 7 and, thus, relative to the end of the cannula emerging at the projection 7 from the body 2 which is provided for the connection to the supply line 3.

A thin protective skin 8 is provided in the area of the contact surface 6 for covering the annular space 4 in order to prevent the penetration of germs.

When looking at the drawing, it is readily apparent that any bending forces which are transmitted from the insertion end 5 to the point A are gradually transferred to the point B. The same is true for the torsional forces which occur when the cannula is inserted and when the catheter is placed in a patient. Any bending forces acting on the insertion end 5 are gradually and partially converted in point B into torsional forces.

While specific embodiments of the invention have been shown and described in detail to illustrate the inventive principles, it will be understood that the invention may be embodied otherwise without departing from such principles.

I claim:

1. An infusion catheter comprising a cannula and a body of synthetic material, wherein the cannula is embedded in the body, the cannula having a first end and a second end, wherein the first end is connected to a supply line and the second end forms an insertion end, wherein the body has a relieving groove in an area thereof where the insertion end of the cannula extends out from the body, wherein the relieving groove is configured as an annular space having an axis, wherein the axis of the annular space approximately coincides with the cannula, such that the annular space extends around the insertion end of the cannula, wherein the body has a contact surface which in a position of use rests on a patient, wherein the insertion end of the cannula extends out from the contact surface, the body comprising a projection extending essentially parallel to the contact surface, wherein the first end connected to the supply line emerges from the body at the projection, wherein the annular space extends into the body starting at the contact surface, wherein the body has a surface located opposite the contact surface, wherein the annular space extends from the contact surface essentially to the opposite surface of the body, and wherein the annular space is shorter only where the cannula is located.

2. The infusion catheter according to claim 1, wherein the cannula extends within the body approximately at a 90° angle.

3. The infusion catheter according to claim 1, further comprising a thin protective skin placed on the annular space for closing the annular space.

* * * * *